United States Patent [19]

Walter

[11] Patent Number: 4,533,735

[45] Date of Patent: Aug. 6, 1985

[54] PROCESS FOR PREPARING ANTIBACTERIAL COMPOUNDS

[75] Inventor: Thomas J. Walter, Baton Rouge, La.

[73] Assignee: Ethyl Corporation, Richmond, Va.

[21] Appl. No.: 495,977

[22] Filed: May 19, 1983

Related U.S. Application Data

[63] Continuation-in-part of Ser. No. 300,046, Sep. 8, 1981, Pat. No. 4,405,792.

[51] Int. Cl.³ .................................... C07D 215/16
[52] U.S. Cl. ............................................ 546/156
[58] Field of Search ..................................... 546/156

[56] References Cited

U.S. PATENT DOCUMENTS

| | | | |
|---|---|---|---|
| 3,542,851 | 11/1970 | Patchett et al. | 546/156 |
| 3,753,993 | 8/1973 | Lesher et al. | 546/156 |
| 3,966,743 | 6/1976 | Berger et al. | 424/258 |
| 3,970,662 | 7/1976 | Carabateas et al. | |
| 3,994,903 | 11/1976 | Carabateas et al. | |
| 4,079,058 | 3/1978 | Ackermann | 546/156 |
| 4,118,557 | 10/1978 | Lesher | 542/420 |
| 4,146,625 | 3/1979 | Lee | 546/156 |
| 4,292,317 | 9/1981 | Pesson | 546/156 |

Primary Examiner—Ethel G. Love
Attorney, Agent, or Firm—Donald L. Johnson; John F. Sieberth; Patricia J. Hogan

[57] ABSTRACT

4-(4-Halo-3-nitrophenyl)pyridines, useful as intermediates in the synthesis of antibacterial 1-alkyl-1,4-dihydro-4-oxo-7-pyridinyl-3-quinolinecarboxylic acids, are obtained by nitrating 4-(4-halophenyl)pyridines. The 4-(4-halo-3-nitrophenyl)pyridines may be converted to the antibacterial agents by reducing them to 4-(3-aminophenyl)pyridines and then subjecting the amino compounds to suitable known reactions.

9 Claims, No Drawings

PROCESS FOR PREPARING ANTIBACTERIAL COMPOUNDS

CROSS-REFERENCE TO RELATED APPLICATION

This application is a continuation-in-part of copending application Ser. No. 300,046, filed Sep. 8, 1981 now U.S. Pat. No. 4,405,792.

FIELD OF THE INVENTION

This invention relates to 4-(4-halo-3-nitrophenyl)-pyridines, processes for synthesizing them, and processes for preparing derivatives therefrom.

BACKGROUND

As disclosed in Sterling Drug's U.S. Pat. No. 3,753,993 (Lesher et al.), 3,907,808 (Lesher and Carabateas), and 4,118,557 (Lesher), it is known that antibacterial 1-alkyl-1,4-dihydro-4-oxo-7-pyridinyl-3-quinolinecarboxylic acids can be prepared from 4-(3-aminophenyl)pyridine. Lesher et al. and Lesher and Carabateas show that their 4-(3-aminophenyl)pyridine is synthesized from 4-(3-nitrophenyl)pyridine, and U.S. Pat. Nos. 3,970,662 (Carabateas and Williams) and 3,994,903 (Carabateas and Brundage) — assigned to the same assignee as Lesher, Lesher et al., and Lesher and Carabateas — indicate that Lesher et al. and Lesher and Carabateas used uneconomical processes for preparing their 4-(3-nitrophenyl) pyridine.

Copending application Ser. No. 300,046, filed Sept. 8, 1981, in the name of Thomas J. Walter, discloses a desirable process for preparing 4-(chlorophenyl)pyridines, including 4-(3-chlorophenyl)pyridine and 4-(4-chlorophenyl)pyridine, and also teaches that these compounds are useful as intermediates in the synthesis of the antibacterial products of Lesher et al. and Lesher and Carabateas.

SUMMARY OF INVENTION

An object of this invention is to provide a novel, economical process for preparing 4-(3-aminophenyl)-pyridines.

Another object is to provide such a process utilizing 4-(4-halophenyl)pyridines.

Still another object is to provide such a process wherein the 4-(4-(halophenyl)pyridine is converted to a 4-(3-aminophenyl)pyridine via a novel intermediate, a 4-(4-halo-3-nitrophenyl)pyridine.

A further object is to provide a novel process for preparing 1-alkyl-1,4-dihydro-4-oxo-7-pyridinyl-3-quinolinecarboxylic acids from a 4-(4-halophenyl)pyridine.

These and other objects are attained by nitrating a 4-(4-halophenyl)pyridine to form a 4-(4-halo-3-nitrophenyl)pyridine, reducing the product to a 4-(3-aminophenyl)pyridine, and, when appropriate, converting the 4-(3-aminophenyl)pyridine to a desired derivative, such as a 1-alkyl-1,4-dihydro-4-oxo-7-pyridinyl-3-quinolinecarboxylic acid or an intermediate thereof.

DETAILED DESCRIPTION

The 4-(4-halophenyl)pyridines utilizable in the practice of the invention are compounds corresponding to the formula:

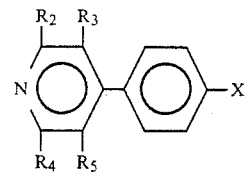

Wherein X is halo, i.e., chloro, bromo, or iodo, and $R_2$, $R_3$, $R_4$, and $R_5$ are independently selected from hydrogen and innocuous substituents, such as alkyl, cycloalkyl, aralkyl, aryl, and alkaryl groups, optionally bearing halo, hydroxy, or amino substituents and/or optionally joined to the pyridine ring by an ether linkage; halo; cyano; carboxyl; carbalkoxy; carbamyl; nitrogen-containing heterocyclic groups, etc. — any aliphatic groups generally containing 1-6 carbons arranged in straight or branched chains. This ingredient, when not available commercially, may be prepared by any suitable technique, e.g., the process taught in the aforementioned copending application Ser. No. 300,046, the teachings of which are incorporated herein by reference. The preferred 4-(4-halophenyl)pyridine is 4-(4-chlorophenyl)pyridine.

The 4-(4-halophenyl)pyridine may be nitrated by any suitable conventional technique, e.g., by reaction with a mixture of concentrated nitric and sulfuric acids, as taught in March, Advanced Organic Chemistry, Second Edition, McGraw-Hill Book Company, New York, 1977, pages 474–476, the teachings of which are incorporated herein by reference. As indicated above, nitration of the 4-(4-halophenyl)pyridine results in the formation of a 4-(4-halo-3-nitrophenyl)pyridine, which may or may not have substituents on the pyridine ring, depending on the starting material employed. When the 4-(4-halophenyl)pyridine starting material is the preferred 4-(4-chlorophenyl)pyridine, there are no substituents on the pyridine ring, of course, and the product of the nitration step is 4-(4-chloro-3-nitrophenyl)pyridine.

The product of the nitration reaction may be reduced to a 4-(3-aminophenyl)pyridine by any suitable conventional means, e.g., by catalytic hydrogenation; use of a reducing agent, such as zinc or iron, in conjunction with dilute acid, etc., as taught in March, Advanced Organic Chemistry, Second Edition, McGraw-Hill, New York, 1977, pages 1125–1126, the teachings of which are incorporated herein by reference. As in the nitration reaction, the product of the reaction may or may not have substituents on the pyridine ring, depending on the starting material employed. However, when the starting material has reducible substituents on the pyridine ring, they are apt to be removed or altered by the reaction.

The 4-(3-aminophenyl)pyridine formed by the process of the invention may be used in any of the applications in which such compounds are known to have utility. However, they are particularly useful in the synthesis of the antibacterial 1-alkyl-1,4-dihydro-4-oxo-7-pyridinyl-3-quinolinecarboxylic acids of Lesher, Lesher et al., and Lesher and Carabateas, i.e., compounds corresponding to the formula:

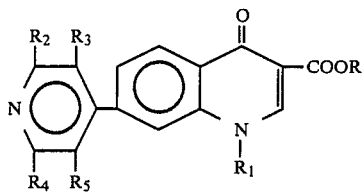

wherein R is hydrogen or alkyl, $R_1$ is alkyl, haloalkyl, or hydroxyalkyl, and $R_2$, $R_3$, $R_4$, and $R_5$ have the same definitions as given above — any aliphatic groups generally containing 1–6 carbons arranged in straight or branched chains.

In the production of the aforementioned antibacterial agents or intermediates thereof, the 4-(3-aminophenyl)-pyridines are subjected to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to a 1-alkyl-1,4-dihydro-4-oxo-7-(4-pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

When an acylated 4-(3-aminophenyl)pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid — a process which leads to a high yield of 4-(3-aminophenyl)pyridine at 60°–70° C. but which produces substantial yields of 4-(3-acetamidophenyl)pyridine when conducted for a sufficient time at temperatures near 80° C. Alternatively and more efficiently, 4-(3-acetamidophenyl)pyridine can be produced by including acetic anhydride in the reduction recipe.

The following examples are given to illustrate the invention and are not intended as a limitation thereof.

EXAMPLE I

A 9.38 g (49.5 mmol) portion of 4-(4-chlorophenyl)pyridine was taken up in 10 ml of concentrated sulfuric acid at about 5°–10° C. A mixture of 4.67 g (52.0 mmols) of concentrated nitric acid in 5 ml of sulfuric acid was added over 30 minutes while maintaining the temperature at 5°–10° C. After the addition was complete, the cooling bath was removed and the reaction was agitated at room temperature for 2.5 hours. The reaction mixture was then diluted with water, and 50% aqueous caustic was added until the pH was greater than 10.

The solids were filtered, washed thoroughly with water, and dried to produce 11.48 g of crude product. The crude product was taken up in 75 ml of hot toluene and filtered through a one-inch layer of diatomaceous earth. The flask and diatomaceous earth were rinsed with hot toluene portions totaling 25 ml. To the combined toluene fractions were added 200 ml of n-hexane. Crystals formed on addition of the hexane. The mixture was cooled to 0° C. The solids were filtered, washed sparingly with cold hexane, and dried. A total of 9.7 g (84%) of buff-colored 4-(4-chloro-3-nitrophenyl) pyridine having a melting point of 110°–111° C. was obtained.

EXAMPLE II

A Paar shaker bottle was charged with 0.2 g (0.85 mmol) of 4-(4-chloro-3-nitrophenyl)pyridine, 0.07 g (0.85 mmol) of sodium acetate, 0.02 g of 5% palladium-on-carbon, and 3 ml of glacial acetic acid. It was then charged with hydrogen to 40 psi, and the shaker was turned on. The reaction mixture was heated to 60°–70° C. and maintained at that temperature for two hours, after which the reaction was stopped and the catalyst removed by filtration. To the filtrate was added water and then 50% aqueous caustic to a pH greater than 7. The reaction mixture was extracted with methylene chloride. The methylene chloride fraction was washed, dried, and evaporated. Analysis of the reaction mixture showed that the process resulted in an 83% yield of 4-(3-aminophenyl)pyridine.

EXAMPLE III

Example II was repeated except that a temperature near 80° C. was employed, and the reaction was run longer. The process resulted in a 40% yield of 4-(3-acetamidophenyl)pyridine.

EXAMPLE IV

A Paar shaker bottle was charged with 0.5 g (2.13 mmols) of 4-(4-chloro-3-nitrophenyl)pyridine, 0.18 g (2.23 mmols) of powdered anhydrous sodium acetate, 0.33 g (3.2 mmols) of acetic anhydride, 0.025 g of 5% palladium-on-carbon, and 10 ml of glacial acetic acid. The bottle was then charged with hydrogen to 45 psi, heated at 80° C., and shaken for 6 hours. The reaction mixture was cooled and filtered. Water was added to the filtrate, followed by 50% caustic to a pH greater than 10. The mixture was extracted with methylene chloride. The methylene chloride fraction was washed and dried and the solvent evaporated to produce 0.34 g (76%) of crude solid, which was assayed and determined to contain 85% of 4-(3-acetamidophenyl)pyridine.

EXAMPLE V

A Paar bottle was charged with 1.5 g (8.82 mmols) of 4-(3-aminophenyl)pyridine, 0.43 g (9.71 mmols) of acetaldehyde, 0.15 g of 5% palladium-on-carbon, 0.3 g of powdered fused sodium acetate, and 20 ml of ethanol. The bottle was then charged with hydrogen to 45 psi, continuously shaken for about 14 hours, and then allowed to stand for approximately 10 additional hours. At this point, the bottle showed a pressure of 38 psi; and the contents were removed, filtered, and washed with ethanol. The ethanol was then evaporated to provide 2.93 g of a pale yellow, oily solid. Analysis of the solid showed it to be crude 3-(4-pyridyl)-N-ethylaniline.

EXAMPLE VI

A mixture of 100 mg of 3-(4-pyridyl)-N-ethylaniline (90% pure) and 108 mg of diethyl ethoxymethylenemalonate was heated at 165° C. for 0.5 hour. Then 2 g of polyphosphoric acid were added to the mixture, and heating was continued for another hour. A solution of 3 g of potassium hydroxide in 40 ml of water was then added to the reaction mixture, bringing it to a pH of 12-13; and the solution was heated on a steam bath for 30 minutes until it became clear. A pinch of activated charcoal was added, and the reaction mixture was stirred while hot for another 10 minutes and filtered. The residue was taken into 20 ml of methanol, heated, and then cooled. Filtration yielded 43 mg of 1-ethyl-1,4-dihydro-4-oxo-7-(4-pyridyl)-3-quinolinecarboxylic acid as a slightly impure white solid. Another 19 mg of the product were found in the filtrate, bringing the total yield to 47%, based on the amount of 3-(4-pyridyl)-N-ethylaniline employed.

It is obvious that many variations may be made in the products and processes set forth above without departing from the spirit and scope of this invention.

I claim:

1. The process wherein:
   (a) a 4-(4-halophenyl)pyridine is nitrated to a 4-(4-halo-3-nitrophenyl)pyridine,
   (b) the 4-(4-halo-3-nitrophenyl)pyridine is reduced to a 4-(3-aminophenyl)pyridine,
   (c) the 4-(3-aminophenyl)pyridine is reacted with a dialkyl ethoxymethylenemalonate to form a dialkyl 3-(4-pyridyl)anilinomethylenemalonate,
   (d) the dialkyl 3-(4-pyridyl)anilinomethylenemalonate is cyclized to an alkyl 1,4-dihydro-4-oxo-7-(4-pyridyl)-3-quinolinecarboxylate,
   (e) the alkyl 1,4-dihydro-4-oxo-7-(4-pyridyl)-3-quinolinecarboxylate is N-alkylated to an alkyl 1-alkyl-1,4-dihydro-4-oxo-7-(4-pyridyl)-3-quinolinecarboxylate, and
   (f) the alkyl 1-alkyl-1,4-dihydro-4-oxo-7-(4-pyridyl)-3-quinolinecarboxylate is hydrolyzed to a 1-alkyl-1,4-dihydro-4-oxo-7-(4-pyridyl)-3-quinolinecarboxylic acid.

2. The process of claim 1 wherein the 4-(4-halophenyl)-pyridine is 4-(4-chlorophenyl)pyridine.

3. The process of claim 1 wherein the 4-(4-halophenyl)pyridine is 4-(4-chlorophenyl)pyridine, and the alkyl 1,4-dihydro-4-oxo-7-(4-pyridyl)-3-quinolinecarboxylate is N-alkylated to an alkyl 1-ethyl-1,4-dihydro-4-oxo-7-(pyridyl)-3-quinolinecarboxylate.

4. The process wherein:
   (a) a 4-(4-halophenyl)pyridine is nitrated to a 4-(4-halo-3-nitrophenyl)pyridine,
   (b) the 4-(4-halo-3-nitrophenyl)pyridine is reduced to a 4-(3-aminophenyl)pyridine,
   (c) the 4-(3-aminophenyl)pyridine is converted to a 3-(4-pyridyl)-N-alkylaniline,
   (d) the 3-(4-pyridyl)-N-alkylaniline is reacted with a dialkyl ethoxymethylenemalonate to form a dialkyl 3-(4-pyridyl)-N-alkylanilinomethylenemalonate,
   (e) the dialkyl 3-(4-pyridyl)-N-alkylanilinomethylenemalonate is cyclized to an alkyl 1-alkyl-1,4-dihydro-4-oxo-7-(4-pyridyl)-3-quinolinecarboxylate, and
   (f) the alkyl 1-alkyl-1,4-dihydro-4-oxo-7-(4-pyridyl)-3-quinolinecarboxylate is hydrolyzed to a 1-alkyl-1,4-dihydro-4-oxo-7-(4-pyridyl)-3-quinolinecarboxylic acid.

5. The process of claim 4 wherein the 4-(3-aminophenyl)-pyridine is converted to the 3-(4-pyridyl)-N-alkylaniline by reductive alkylation.

6. The processs of claim 4 wherein the 4-(3-aminophenyl) pyridine is converted to the 3-(4-pyridyl)-N-alkylaniline by sequential acylation and reduction.

7. The process of claim 4 wherein the 4-(4-halophenyl)pyridine is 4-(4-chlorophenyl)pyridine.

8. The process of claim 4 wherein the 4-(4-halophenyl)-pyridine is 4-(4-chlorophenyl)pyridine and the 4-(3-aminophenyl)-pyridine is converted to a 3-(4-pyridyl)-N-ethylaniline.

9. The process wherein (a) a 4-(4-halophenyl)pyridine is nitrated to a 4-(4-halo-3-nitrophenyl)pyridine,
   (b) the 4-(4-halo-3-nitrophenyl)pyridine is reduced to a 4-(3-aminophenyl)pyridine, and (c) the 4-(3-aminophenyl)pyridine is converted to a 1-alkyl-1,4-dihydro-4-oxo-7-(4-pyridyl)-3-quinolinecarboxylic acid.

* * * * *